(12) United States Patent
Thompson et al.

(10) Patent No.: US 9,155,613 B2
(45) Date of Patent: Oct. 13, 2015

(54) METHODS FOR CREATING FOAM-LIKE TEXTURE

(71) Applicant: Allergan, Inc., Irvine, CA (US)

(72) Inventors: Jordan Thompson, Chino Hills, CA (US); Alexei Goraltchouk, Rensselaer, NY (US); Kevin Ma, Scotts Valley, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/174,133

(22) Filed: Feb. 6, 2014

(65) Prior Publication Data

US 2014/0156002 A1    Jun. 5, 2014

Related U.S. Application Data

(62) Division of application No. 13/297,120, filed on Nov. 15, 2011, now Pat. No. 8,679,279.

(60) Provisional application No. 61/414,250, filed on Nov. 16, 2010.

(51) Int. Cl.

| A61F 2/12 | (2006.01) |
|---|---|
| B29C 43/02 | (2006.01) |
| A61L 27/34 | (2006.01) |
| A61L 27/56 | (2006.01) |
| B29C 59/00 | (2006.01) |
| B29C 59/02 | (2006.01) |
| A61F 2/00 | (2006.01) |
| B29L 31/00 | (2006.01) |

(Continued)

(52) U.S. Cl.
CPC . *A61F 2/12* (2013.01); *A61L 27/34* (2013.01); *A61L 27/56* (2013.01); *B29C 43/02* (2013.01); *B29C 59/005* (2013.01); *B29C 59/02* (2013.01); *A61F 2/0077* (2013.01); *A61F 2240/001* (2013.01); *A61L 2400/08* (2013.01); *A61L 2400/18* (2013.01); *A61L 2430/04* (2013.01); *B29C 41/14* (2013.01); *B29C 65/483* (2013.01); *B29C 66/71* (2013.01); *B29C 66/727* (2013.01); *B29L 2031/7532* (2013.01)

(58) Field of Classification Search
None
See application file for complete search history.

(56) References Cited

U.S. PATENT DOCUMENTS

| 2,805,208 A | 9/1957 | Roche |
|---|---|---|
| 3,189,921 A | 6/1965 | Pangman |

(Continued)

FOREIGN PATENT DOCUMENTS

| CA | 2049377 A1 | 3/1992 |
|---|---|---|
| EP | 0230672 | 8/1987 |

(Continued)

OTHER PUBLICATIONS

Brauker et al., "Neovascularization of synthetic membranes directed by membrane microarchitecture", Journal of Biomedical Materials Research, 1995, pp. 1517-1524, vol. 29, John Wiley & Sons, Inc.

(Continued)

*Primary Examiner* — David H Willse
*Assistant Examiner* — Javier Blanco
(74) *Attorney, Agent, or Firm* — Linda Allyson Nassif (57) ABSTRACT

Methods for creating a foam-like texture on an implantable material are provided. More particularly, methods for creating foam-like texture on implantable silicone materials are provided.

13 Claims, 6 Drawing Sheets

(51) Int. Cl.
B29C 65/00 (2006.01)
B29C 41/14 (2006.01)
B29C 65/48 (2006.01)

(56) References Cited

U.S. PATENT DOCUMENTS

| | | |
|---|---|---|
| 3,293,663 A | 12/1966 | Cronin |
| 3,366,975 A | 2/1968 | Pangman |
| 3,559,214 A | 2/1971 | Pangman |
| 3,600,718 A | 8/1971 | Boone |
| 3,665,520 A | 5/1972 | Perras |
| 3,700,380 A | 10/1972 | Kitrilakis |
| 3,852,832 A | 12/1974 | McGhan |
| 3,934,274 A | 1/1976 | Hartley, Jr. |
| 4,010,495 A | 3/1977 | Horvath |
| 4,034,751 A | 7/1977 | Hung |
| 4,157,085 A | 6/1979 | Austad |
| 4,197,948 A | 4/1980 | Amberg et al. |
| 4,231,979 A | 11/1980 | White |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein |
| 4,499,211 A | 2/1985 | Walch |
| 4,531,244 A | 7/1985 | Hamas |
| 4,573,999 A | 3/1986 | Netto |
| 4,584,324 A | 4/1986 | Baumann et al. |
| 4,592,755 A | 6/1986 | Penton |
| 4,610,690 A | 9/1986 | Tiffany |
| 4,636,213 A | 1/1987 | Pakiam |
| 4,643,733 A | 2/1987 | Becker |
| 4,647,618 A | 3/1987 | Baumann et al. |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl et al. |
| 4,740,208 A | 4/1988 | Cavon |
| 4,772,285 A | 9/1988 | Ksander et al. |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl |
| 4,803,025 A | 2/1989 | Brockmeyer |
| 4,828,560 A | 5/1989 | Heyler, III |
| 4,840,628 A | 6/1989 | Cavon |
| 4,841,992 A | 6/1989 | Sasaki et al. |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox, Jr. |
| 4,950,292 A | 8/1990 | Audretsch |
| 4,955,907 A | 9/1990 | Ledergerber |
| 4,955,909 A | 9/1990 | Ersek |
| 4,960,425 A | 10/1990 | Yan et al. |
| 4,965,430 A | 10/1990 | Curtis et al. |
| 4,969,899 A | 11/1990 | Cox, Jr. |
| 5,002,572 A | 3/1991 | Picha |
| 5,007,929 A | 4/1991 | Quaid |
| 5,007,940 A | 4/1991 | Berg |
| 5,011,494 A | 4/1991 | von Recum et al. |
| 5,022,942 A | 6/1991 | Yan et al. |
| 5,026,394 A | 6/1991 | Baker |
| 5,034,422 A | 7/1991 | Triolo et al. |
| 5,035,249 A | 7/1991 | Sasaki et al. |
| 5,092,348 A | 3/1992 | Dubrul |
| 5,092,882 A | 3/1992 | Lynn |
| 5,104,409 A | 4/1992 | Baker |
| 5,116,387 A | 5/1992 | Berg |
| 5,135,959 A | 8/1992 | Hill |
| 5,146,933 A | 9/1992 | Boyd |
| 5,147,398 A | 9/1992 | Lynn et al. |
| 5,158,571 A | 10/1992 | Picha |
| 5,158,573 A | 10/1992 | Berg |
| 5,171,269 A | 12/1992 | Bark |
| 5,185,297 A | 2/1993 | Park et al. |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,282,856 A | 2/1994 | Ledergerber |
| 5,296,069 A | 3/1994 | Robert |
| 5,348,788 A | 9/1994 | White |
| 5,354,338 A | 10/1994 | Ledergerber |
| 5,358,521 A | 10/1994 | Shane |
| 5,376,117 A | 12/1994 | Pinchuk et al. |
| 5,383,929 A | 1/1995 | Ledergerber |
| 5,437,824 A | 8/1995 | Carlisle et al. |
| 5,441,919 A | 8/1995 | Park et al. |
| 5,447,535 A | 9/1995 | Muller |
| 5,455,100 A | 10/1995 | White |
| 5,480,430 A | 1/1996 | Carlisle et al. |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iversen et al. |
| 5,534,023 A | 7/1996 | Henley |
| 5,545,217 A | 8/1996 | Offray et al. |
| 5,545,220 A | 8/1996 | Andrews et al. |
| 5,549,671 A | 8/1996 | Waybright et al. |
| 5,571,179 A | 11/1996 | Manders et al. |
| RE35,391 E | 12/1996 | Brauman |
| 5,589,176 A | 12/1996 | Seare, Jr. |
| 5,605,693 A | 2/1997 | Seare, Jr. |
| 5,607,473 A | 3/1997 | Weber-Unger et al. |
| 5,624,674 A | 4/1997 | Seare, Jr. |
| 5,630,843 A | 5/1997 | Rosenberg |
| 5,630,844 A | 5/1997 | Dogan et al. |
| 5,653,755 A | 8/1997 | Ledergerber |
| 5,658,330 A | 8/1997 | Carlisle et al. |
| 5,674,285 A | 10/1997 | Quaid |
| 5,681,572 A | 10/1997 | Seare, Jr. |
| 5,779,734 A | 7/1998 | Ledergerber |
| 5,798,065 A | 8/1998 | Picha |
| 5,824,081 A | 10/1998 | Knapp et al. |
| 5,843,189 A | 12/1998 | Perouse |
| 5,855,588 A | 1/1999 | Young |
| 5,871,497 A | 2/1999 | Young |
| 5,895,423 A | 4/1999 | Becker et al. |
| 5,935,164 A | 8/1999 | Iversen |
| 5,961,552 A | 10/1999 | Iversen et al. |
| 5,964,803 A | 10/1999 | Iversen et al. |
| 5,965,076 A | 10/1999 | Banks et al. |
| 5,984,943 A | 11/1999 | Young |
| 5,993,716 A | 11/1999 | Draenert |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura, Jr. |
| 6,113,634 A | 9/2000 | Weber-Unger et al. |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg et al. |
| 6,214,045 B1 | 4/2001 | Corbitt, Jr. et al. |
| 6,214,926 B1 | 4/2001 | Winn et al. |
| 6,315,796 B1 | 11/2001 | Eaton |
| 6,340,648 B1 | 1/2002 | Imura et al. |
| 6,387,133 B1 | 5/2002 | Perouse |
| 6,432,138 B1 | 8/2002 | Offray et al. |
| 6,464,726 B1 | 10/2002 | Heljenek |
| 6,520,989 B1 | 2/2003 | Eaton |

(56) References Cited

U.S. PATENT DOCUMENTS

| | | |
|---|---|---|
| 6,531,523 B1 | 3/2003 | Davankov et al. |
| 6,544,287 B1 | 4/2003 | Johnson et al. |
| 6,602,452 B2 | 8/2003 | Schuessler |
| 6,605,116 B2 | 8/2003 | Falcon et al. |
| 6,638,308 B2 | 10/2003 | Corbitt, Jr. et al. |
| 6,673,285 B2 | 1/2004 | Ma |
| 6,692,527 B1 | 2/2004 | Bellin et al. |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt, Jr. et al. |
| 6,900,055 B1 | 5/2005 | Fuller et al. |
| 6,913,626 B2 | 7/2005 | McGhan |
| 6,916,339 B1 | 7/2005 | Missana et al. |
| 6,921,418 B2 | 7/2005 | Ledergerber |
| 6,932,840 B1 | 8/2005 | Bretz |
| 7,081,135 B2 | 7/2006 | Smith et al. |
| 7,081,136 B1 | 7/2006 | Becker |
| 7,105,116 B2 | 9/2006 | Bellin et al. |
| 7,169,180 B2 | 1/2007 | Brennan |
| 7,192,450 B2 | 3/2007 | Brauker et al. |
| 7,244,270 B2 | 7/2007 | Lesh |
| 7,309,232 B2 | 12/2007 | Rutherford et al. |
| 7,323,208 B2 | 1/2008 | Ma et al. |
| 7,476,249 B2 | 1/2009 | Frank |
| 7,520,896 B2 | 4/2009 | Benslimane |
| 7,547,393 B2 | 6/2009 | Ramaswamy et al. |
| 7,625,405 B2 | 12/2009 | Purkait |
| 7,632,228 B2 | 12/2009 | Brauker et al. |
| 7,632,291 B2 | 12/2009 | Stephens et al. |
| 7,641,688 B2 | 1/2010 | Lesh |
| 7,645,475 B2 | 1/2010 | Prewett |
| 7,758,788 B2 | 7/2010 | Job |
| 7,867,061 B2 | 1/2011 | Elshout |
| 8,202,317 B2 | 6/2012 | Becker |
| 8,313,527 B2 | 11/2012 | Powell et al. |
| 8,487,012 B2 | 7/2013 | Goraltchouk et al. |
| 8,728,159 B2 | 5/2014 | Kim |
| 8,765,039 B1 | 7/2014 | Ledergerber |
| 2002/0038147 A1 | 3/2002 | Miller, III |
| 2002/0193885 A1 | 12/2002 | Legeay et al. |
| 2003/0036803 A1 | 2/2003 | McGhan |
| 2003/0093151 A1 | 5/2003 | Zhang |
| 2003/0105469 A1 | 6/2003 | Karmon |
| 2003/0205846 A1 | 11/2003 | Bellin |
| 2003/0208269 A1 | 11/2003 | Eaton et al. |
| 2004/0010225 A1 | 1/2004 | Schuessler |
| 2004/0115241 A1 | 6/2004 | Calhoun et al. |
| 2004/0127985 A1 | 7/2004 | Bellin et al. |
| 2004/0143327 A1 | 7/2004 | Ku |
| 2004/0148024 A1 | 7/2004 | Williams |
| 2004/0153151 A1 | 8/2004 | Gonzales de Vicente |
| 2004/0213986 A1 | 10/2004 | Kim et al. |
| 2005/0055093 A1 | 3/2005 | Brennan |
| 2005/0070124 A1 | 3/2005 | Miller et al. |
| 2005/0112169 A1 | 5/2005 | Brauker et al. |
| 2005/0175702 A1 | 8/2005 | Muller-Schulte |
| 2005/0196452 A1 | 9/2005 | Boyan et al. |
| 2005/0216094 A1 | 9/2005 | Prewett |
| 2005/0251083 A1 | 11/2005 | Carr-Brendel et al. |
| 2006/0002810 A1 | 1/2006 | Grohowski |
| 2006/0036266 A1 | 2/2006 | Sulmanidze et al. |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma et al. |
| 2006/0259133 A1 | 11/2006 | Sowinski et al. |
| 2007/0093911 A1 | 4/2007 | Fricke et al. |
| 2007/0104693 A1 | 5/2007 | Quijano et al. |
| 2007/0104695 A1 | 5/2007 | Quijano et al. |
| 2007/0116735 A1 | 5/2007 | Calhoun et al. |
| 2007/0135916 A1 | 6/2007 | Maxwell et al. |
| 2007/0154525 A1 | 7/2007 | Calhoun et al. |
| 2007/0190108 A1 | 8/2007 | Datta et al. |
| 2007/0198085 A1 | 8/2007 | Benslimane |
| 2008/0009830 A1 | 1/2008 | Fujimoto et al. |
| 2008/0071371 A1 | 3/2008 | Elshout |
| 2008/0075752 A1 | 3/2008 | Ratner et al. |
| 2008/0095823 A1 | 4/2008 | Williams et al. |
| 2008/0154366 A1 | 6/2008 | Frank |
| 2008/0241212 A1 | 10/2008 | Moses et al. |
| 2008/0268019 A1 | 10/2008 | Badylak et al. |
| 2008/0312739 A1 | 12/2008 | Agerup et al. |
| 2009/0045166 A1 | 2/2009 | Li |
| 2009/0082864 A1 | 3/2009 | Chen et al. |
| 2009/0087641 A1 | 4/2009 | Favis et al. |
| 2009/0093878 A1 | 4/2009 | Glicksman |
| 2009/0118829 A1 | 5/2009 | Powell et al. |
| 2009/0125107 A1 | 5/2009 | Maxwell |
| 2009/0169716 A1 | 7/2009 | Linhardt et al. |
| 2009/0198331 A1 | 8/2009 | Kesten et al. |
| 2009/0198332 A1 | 8/2009 | Becker |
| 2009/0198333 A1 | 8/2009 | Becker |
| 2010/0042211 A1 | 2/2010 | Van Epps et al. |
| 2010/0042212 A1 | 2/2010 | Van Epps et al. |
| 2010/0292790 A1 | 11/2010 | Stroumpoulis et al. |
| 2011/0035004 A1 | 2/2011 | Maxwell |
| 2011/0054605 A1 | 3/2011 | Becker |
| 2011/0093069 A1 | 4/2011 | Goraltchouk et al. |
| 2011/0106249 A1 | 5/2011 | Becker |
| 2011/0117267 A1 | 5/2011 | Powell et al. |
| 2011/0196488 A1 | 8/2011 | Goraltchouk et al. |
| 2011/0196489 A1 | 8/2011 | Van Epps et al. |
| 2011/0276133 A1 | 11/2011 | Liu et al. |
| 2011/0276134 A1 | 11/2011 | Manesis et al. |
| 2011/0278755 A1 | 11/2011 | Liu et al. |
| 2011/0282444 A1 | 11/2011 | Liu et al. |
| 2011/0309541 A1 | 12/2011 | Thompson et al. |
| 2011/0313073 A1 | 12/2011 | Goraltchouk et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077012 A1 | 3/2012 | Liu et al. |
| 2012/0077891 A1 | 3/2012 | Liu et al. |
| 2012/0101574 A1 | 4/2012 | Goraltchouk et al. |
| 2012/0142798 A1 | 6/2012 | Thompson et al. |
| 2012/0245685 A1 | 9/2012 | Yu |
| 2012/0321777 A1 | 12/2012 | Stroumpoulis et al. |
| 2013/0023987 A1 | 1/2013 | Liu et al. |
| 2013/0032962 A1 | 2/2013 | Liu et al. |
| 2013/0053956 A1 | 2/2013 | Powell et al. |
| 2013/0158657 A1 | 6/2013 | Nofrey et al. |

FOREIGN PATENT DOCUMENTS

| | | |
|---|---|---|
| EP | 0315814 A2 | 10/1988 |
| EP | 0332371 A1 | 9/1989 |
| EP | 0522585 | 1/1993 |
| EP | 0710468 B1 | 1/2002 |
| EP | 1532942 | 5/2005 |
| EP | 1847369 B1 | 12/2008 |
| FR | 2840617 | 12/2003 |
| GB | 1022736 A | 3/1966 |
| GB | 2225016 A | 5/1990 |
| JP | 2003-062062 | 3/2003 |
| JP | 2007-029717 | 2/2007 |
| MX | 2012012801 A | 5/2014 |
| RU | 2340308 C1 | 12/2008 |
| WO | 9715242 A1 | 5/1997 |
| WO | 9810803 A1 | 3/1998 |
| WO | 9842318 A1 | 10/1998 |
| WO | 0024437 A3 | 5/2000 |
| WO | 0056376 A1 | 9/2000 |
| WO | 2004037318 A2 | 5/2004 |
| WO | 2004062531 A1 | 7/2004 |
| WO | 2005020849 A2 | 3/2005 |
| WO | 2006133366 | 12/2006 |
| WO | 2008001591 A1 | 1/2008 |
| WO | 2009061672 A1 | 5/2009 |
| WO | 2009110917 A1 | 9/2009 |

(56) References Cited

FOREIGN PATENT DOCUMENTS

| | | |
|---|---|---|
| WO | 2011066441 A1 | 6/2011 |
| WO | 2011094155 A2 | 8/2011 |
| WO | 2011097499 A1 | 8/2011 |

OTHER PUBLICATIONS

Brohim et al., "Early Tissue Reaction to Textured Breast Implant Surfaces", Anals of Plastic Surgery, 28(4): 354-362.

Sharkawy et al. "Engineering the tissue which encapsulates subcutaneous implants", II. Plasma—tissue exchange properties, 1998, pp. 586-597, John Wiley & Sons, Inc.

Alvarez, Sonia et al., "Synthesis of Macro/Mesoporous Silica and Carbon Monoliths by Using a Commercial Polyurethane Foam As Sacrificial Template," Materials Letters, 61, 2378-2381 (2007).

Barr, S. et al., "Current Implant Surface Technology: An Examination of Their Nanostructure and Their Influence on Fibroblast Alignment and Biocompatibility," Elastic, 2009, 9, 198-217.

Barnsley, Philip et al., "Textured Surface Breast Implants in the Prevention of Capsular Contracture Among Breast Augmentation Patients: A Meta-Analysis of Randomized Controlled Trials," Plastic and Reconstructive Surgery, 2006, 117(7), 2182-2190.

Inamed Aesthetics Brochure, Directions for Use Style 410 Silicone-Filled Breast Implants (2003).

Ma, Peter, "Scaffolds for tissue fabrication," Materials Today, 2004, 7, 30-40.

Mikes, Antonius et al., "Formation of Highly Porous Biodegradable Scaffolds for Tissue Engineering," Electronic Journal of Biotechnology, 2000, 3(2), 114-119.

Minami, Eliza et al., "The Composition and Behavior of Capsules Around Smooth and Textured Breast Implants in Pigs," Plastic and Reconstructive Surgery, 2006, 118940, 874-884.

Murphy, William, et al., "Salt Fusion: An Approach to Improve Pore Interconnectivity Within Tissue Engineering Scaffolds," Tissue Engineering, vol. 8, Iss. 1, 2004.

Wei, Guobao et al., "Macroporous and Nanofibers Polymer Scaffolds and Polymer/bone-like Apatite Composite Scaffolds Generated by Sugar Spheres," Journal of Biomedical Materials Research Part A, 2006, 306-315.

Zhang, Yuan et al., "Macroporous Alumina Monoliths Prepared by Filling Polymer Foams With Alumina Hydrosols," J. Mater Sci., 44, 931-938 (2009).

OPEN ↑ CLOSED

METHODS FOR CREATING FOAM-LIKE TEXTURE

RELATED APPLICATION

This application is a divisional of U.S. patent application Ser. No. 13/297,120, filed Nov. 15, 2011, which claims priority to U.S. Provisional Patent Application No. 61/414,250, filed Nov. 16, 2010, the entire disclosure of each of these applications being incorporated herein by this reference.

FIELD OF THE INVENTION

The present invention pertains to methods for creating a foam-like texture on an implantable material. More particularly, the present invention relates to methods for creating foam-like texture on implantable silicone materials.

BACKGROUND

Prostheses or implants for augmentation and/or reconstruction of the human body are well known. Capsular contracture is a complication associated with surgical implantation of prostheses, particularly with soft implants, and even more particularly, though certainly not exclusively, with fluid-filled breast implants.

Capsular contracture is believed to be a result of the immune system response to the presence of a foreign material in the body. A normal response of the body to the presence of a newly implanted object, for example a breast implant, is to form a capsule of tissue, primarily collagen fibers, around the implant. Capsular contracture occurs when the capsule begins to contract and squeeze the implant. This contracture can be discomforting or even extremely painful, and can cause distortion of the appearance of the augmented or reconstructed breast. The exact cause of contracture is not known. However, some factors may include bacterial contamination of the implant prior to placement, submuscular versus subglandular placement, and smooth surface implants versus textured surface implants, and bleeding or trauma to the area.

Surface texturing has been shown to reduce capsular contracture when compared to what are known as "smooth" surface implants.

There is still a need for a more optimal surface textured implant that further reduces the potential for capsular contracture. The present invention addresses this need.

SUMMARY OF INVENTION

The present invention pertains to methods for creating a foam-like texture on a material that is suitable for implantation in a mammal.

In one aspect, the present invention provides a method of making a material having a foam-like texture and suitable for implantation in a mammal, the method comprising:
1) applying a texturing material lacking a foam-like texture onto a mandrel of a desired shape;
2) placing a foam-like material over the texturing material;
3) applying pressure to integrate the foam-like material and the texturing material;
4) allowing the foam-like texture to set in the texturing material;
5) removing the foam-like material from the texturing material which has acquired a foam-like texture.

Metal rings may be used to clamp and immobilize the foam-like material as the foam-like material is pressed down on and integrated into the non-solid texturing material; the weight of the metal rings can aid in pressing the foam-like material and the texturing material together. In another variant, a base coat, which may be the same material as the texturing material, may be spread onto the mandrel and solidified before the texturing material is spread onto the base coat.

In another aspect, the present invention provides a method of making a material having a foam-like texture and suitable for implantation in a mammal, the method comprising:
1) applying a texturing material lacking a foam-like texture onto a film coater;
2) placing a foam-like material over the texturing material;
3) applying pressure to integrate the foam-like material and the texturing material;
4) allowing the foam-like texture to set in the texturing material;
5) removing the foam-like material from the texturing material which has acquired a foam-like texture.

A base coat, which may be the same material as the texturing material, may be spread onto the film coater and solidified before the texturing material is spread onto the base coat.

In another aspect, the present invention provides a method of making a material having a foam-like texture and suitable for implantation in a mammal, the method comprising:
1) applying pressure to integrate a first texturing material lacking a foam-like texture and a foam-like material;
2) allowing the foam-like texture to set in the first texturing material;
3) applying pressure to integrate a second texturing material with the composite of the first texturing material and the foam-like material;
4) allowing the foam-like texture to set in the second texturing material;
5) removing the foam-like material from the texturing materials which have acquired a foam-like texture.

The present invention also provides a method for creating one or more foam-like-textured surfaces on a breast prosthesis or implant. A textured material, having the desired dimensions, that acquires a foam-like texture through any of the novel methods described above, can be bonded, by a suitable, biocompatible adhesive, to a smooth shell breast prosthesis, to produce a breast prosthesis having a foam-like-textured surface.

BRIEF DESCRIPTION OF THE DRAWINGS

The present invention may be more clearly understood and certain aspects and advantages thereof better appreciated with reference to the following Detailed Description when considered with the accompanying Drawings of which.

DETAILED DESCRIPTION

The present invention pertains to methods for creating a foam-like texture on an implantable material. More particularly, the present invention relates to methods for creating foam-like texture on implantable silicone materials. Even more specifically, the present invention relates to methods for creating polyurethane-foam-like texture on implantable silicone materials.

The present invention also relates to methods for creating one or more foam-like texture surfaces on breast prostheses or implants.

As used herein, "foam-like texture" refers to texture that is characterized by interconnected pores or the like, or texture that resembles or approximates such a texture.

As used herein, "texturing material" refers to a substantially non-biodegradable polymeric material that acquires a foam-like texture through the novel methods disclosed herein. In the "EXAMPLES" section, silicone is the texturing material. Other examples of texturing material include, but are not limited to: polyurethane, polyesters, polyolefins, polyisobutylene, ethylene-alphaolefin copolymers, acrylic polymers and copolymers, ethylene-co-vinylacetate, polybutylmethacrylate, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polyacrylonitrile, polyvinyl ketones, polyvinyl aromatics (e.g., polystyrene), polyvinyl esters (e.g., polyvinyl acetate), copolymers of vinyl monomers with each other and olefins (e.g., ethylene-methyl methacrylate copolymers, acrylonitrile-styrene copolymers, ABS resins, and ethylene-vinyl acetate copolymers), polyamides (e.g., Nylon 66 and polycaprolactam), alkyd resins, polycarbonates, polyoxymethylenes, polyimides, polyethers, epoxy resins, rayon, ryon-triacetate, cellulose, cellulose acetate, cellulose butyrate, cellulose acetate butyrate, cellophane, cellulose nitrate, cellulose propionate, cellulose ethers, carboxymethyl cellulose, and combinations thereof. The texturing material used for the novel methods disclosed herein can be selected or enhanced based upon considerations such as resistance to acids and bases, mechanical strength, resistance to radiation, such as UV, exposure, and resistance to metal salts or solvents. As used herein, a "base coat" can be of any material that the "texturing material" can be.

As used herein, "foam-like material" refers to a material that has a "foam-like texture" and is used to impart a foam-like texture to a "texturing material" through the novel methods disclosed herein. In the "EXAMPLES" section, polyurethane foam is the foam-like material. The following are other non-limiting examples of foam-like material or material which can be used to make foam-like material: polyethylene, polyethylene vinyl acetate, polystyrene, polyvinyl alcohol, Styrofoam, polyolefin, polyester, polyether, polysaccharide, polyamide, polyacrylate; a material which contains aromatic or aliphatic structures in the backbone, as functionalities, cross-linkers or pendant groups, or a copolymer, terpolymer, or quarternaly polymer thereof; metal, metal foam, ceramic, ceramic foam, and combinations thereof.

Novel methods disclosed herein generally comprise:
1) integrating a texturing material lacking a foam-like texture with a foam-like material by pressing them together;
2) removing the foam-like material from the solidified texturing material which has acquired a foam-like texture.

If the texturing material is a non-solid prior to integration with a foam-like material, the texturing material would be solidified following integration.

In one aspect, the present invention provides a method of making a material having a foam-like texture and suitable for implantation in a mammal, the method comprising:
1) applying a texturing material lacking a foam-like texture onto a mandrel of a desired shape;
2) placing a foam-like material over the texturing material;
3) applying pressure to integrate the foam-like material and the texturing material;
4) allowing the foam-like texture to set in the texturing material;
5) removing the foam-like material from the texturing material which has acquired a foam-like texture.

The above aspect of the present invention is illustrated in examples 1 and 2 in the "EXAMPLES" section. Metal rings may be used to clamp and immobilize the foam-like material as the foam-like material is pressed down on and integrated into the non-solid texturing material; the weight of the metal rings can aid in pressing the foam-like material and the texturing material together. A base coat, which may be the same material as the texturing material, may be spread onto the mandrel and solidified before the texturing material is spread onto the base coat. The step of allowing the foam-like texture to set in the texturing material may comprise solidifying the texturing material, such as by heat-curing.

In another aspect, the present invention provides a method of making a material having a foam-like texture and suitable for implantation in a mammal, the method comprising:
1) applying a texturing material lacking a foam-like texture onto a film coater;
2) placing a foam-like material over the texturing material;
3) applying pressure to integrate the foam-like material and the texturing material;
4) allowing the foam-like texture to set in the texturing material;
5) removing the foam-like material from the texturing material which has acquired a foam-like texture.

The step of allowing the foam-like texture to set in the texturing material may comprise
solidifying the texturing material, such as by heat-curing. A base coat, which may be the same material as the texturing material, may be spread onto the film coater and solidified before the texturing material is spread onto the base coat. This embodiment is illustrated in example 3 in the "EXAMPLES" section.

In another aspect, the present invention provides a method of making a material having a foam-like texture and suitable for implantation in a mammal, the method comprising:

1) applying pressure to integrate a first texturing material lacking a foam-like texture and a foam-like material;
2) allowing the foam-like texture to set in the first texturing material;
3) applying pressure to integrate a second texturing material with the composite of the first texturing material and the foam-like material;
4) allowing the foam-like texture to set in the second texturing material;
5) removing the foam-like material from the texturing materials which have acquired a foam-like texture.

This embodiment is illustrated in examples 4 and 5 in the "EXAMPLES" section.

EXAMPLES

Types of silicones mentioned in the following examples were obtained from NuSil Silicone Technology, Carpinteria, Calif.

Example 1

Uncured Room-Temperature-Vulcanizing ("RTV") silicone, for example, MED-1511, is spread onto a mandrel of a desired shape as a layer having a thickness of 200 μm. A polyurethane foam is placed over the RTV silicone and the mandrel with the aid of metal rings which clamp the foam in place. The weight of the metal rings asserts a force of approximately 30 psi against the polyurethane foam, the RTV silicone and the mandrel. After the RTV silicone is cured, the metal ring and mandrel are removed from the composite of the cured RTV silicone and polyurethane foam. The composite of the cured RTV silicone and polyurethane foam is submerged in hydrochloric acid for five minutes to remove the polyurethane foam. Excess hydrochloric acid is removed by washing in distilled water for two minutes. The resulting product is a silicone material having a foam-like texture.

Example 2

Figure 1:
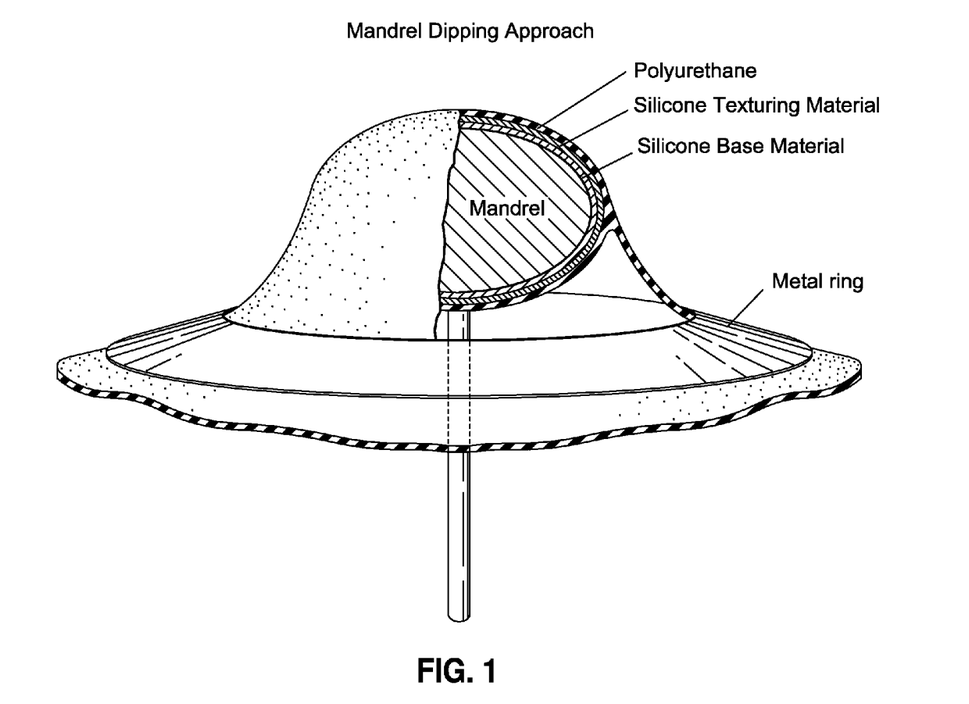
FIG. 1 is a front perspective view and partial cross-section view which reflects an embodiment of the current invention in which a silicone base material is first spread onto a mandrel and cured, then the mandrel is dipped in a silicone texturing material; a piece of polyurethane foam clamped down by metal rings is placed over and pressed down against the silicone texturing material before the silicone texturing material is cured and acquires the texture of the polyurethane foam.

A base coat of uncured High-Temperature-Vulcanizing ("HTV") silicone dispersed in xylene, for example, MED-6400 dispersed in xylene, is spread onto a mandrel and cured (in FIG. 1, the "silicone base material"). The mandrel covered by a base coat is then dipped in a second uncured HTV silicone dispersed in xylene (in FIG. 1, the "silicone texturing material"), for example, MED 6640 in xylene, until the second coat of HTV silicone dispersed in xylene reaches a thickness of (about) 250 μm. Then the xylene is removed from the HTV silicone materials by devolatilization in a fume hood. Next, a piece of polyurethane foam is placed over and pressed down against the HTV-silicone-coated mandrel. One way to apply the polyurethane foam to the HTV-silicone-coated mandrel is to clamp the foam between metal rings (see FIG. 1), then place the exposed portion of the foam that is circumscribed within the rings over the mandrel; the metal rings immobilize the foam to keep it in place and press the foam against the HTV-silicone-coated mandrel. With the polyurethane foam integrated into the second coat of HTV silicone, the second coat of HTV silicone is heat-cured. After the silicone has been cured and acquired the texture of the polyurethane foam, the polyurethane foam is removed by application of acid or hot solvent.

Example 3

Silicone Sheet Approach

Figure 2:
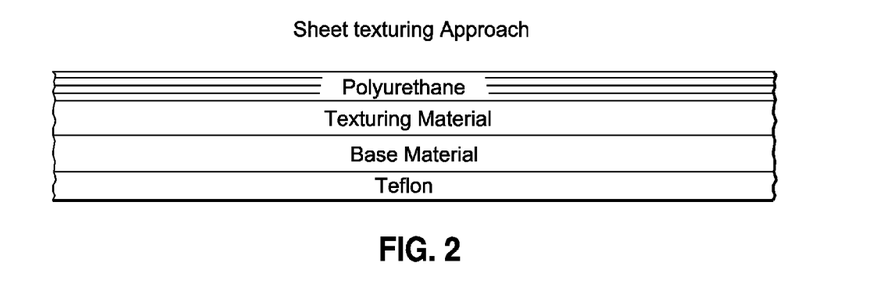
FIG. 2 is an illustration of an embodiment of the current invention in which a base material, which can be a silicone material, is the first layer of material cast onto the Teflon surface of a film coater; the texturing material, which can be a silicone material, is the second layer of material placed on top of the base material and a piece of polyurethane foam is the uppermost material.
Figure 3A:
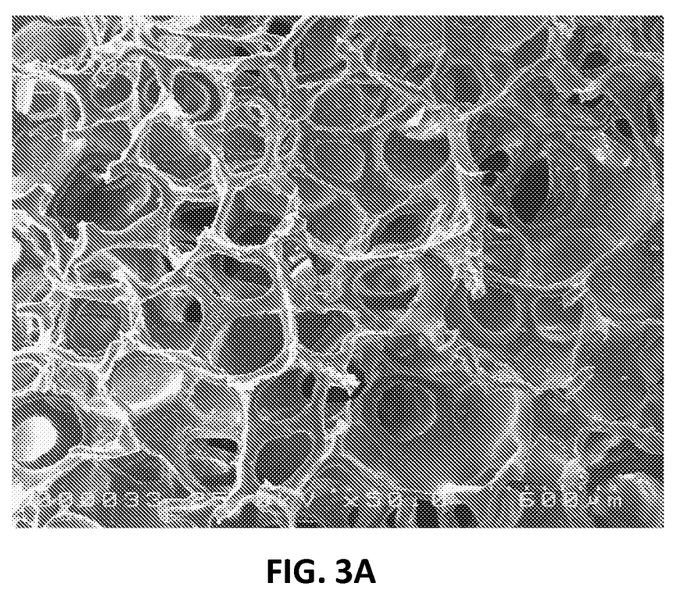
FIGS. 3A & 3B are SEM micrographs of the top view of a silicone material, MED-4815, which has acquired a foam-like texture through the "sheet approach."
Figure 3B:
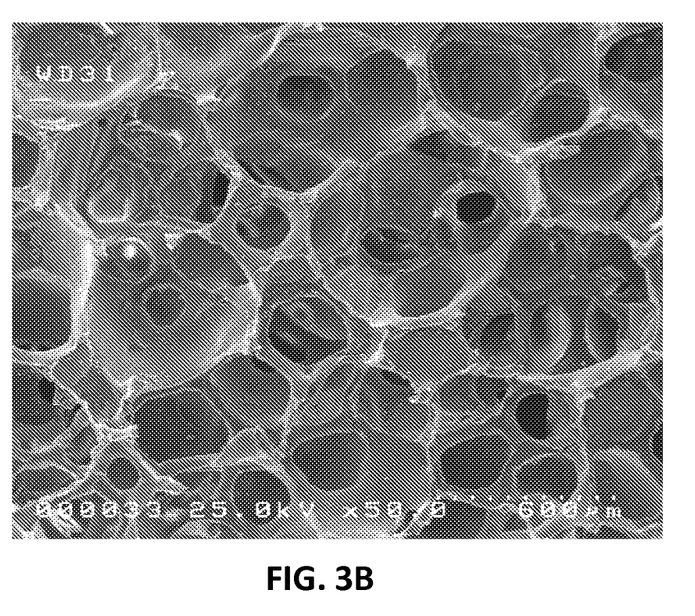

An uncured silicone material (1 mm thick, 5"×5"), such as MED-4815 dispersed in xylene (50 ml, 30% w/w), is cast onto a Teflon sheet on the surface of a film coater. After the film coater creates an even sheet of the silicone, the Teflon sheet is taken off of the film coater and the silicone is cured in an oven at 126° C. for 2 hours. The Teflon sheet with the cured, first layer is then placed back on the film coater. Then, an uncured, second layer of silicone material, which maybe the same material as the cured, first layer, is spread onto the surface of the cured, first layer. The film coater creates an even sheet of the uncured second layer of silicone. The Teflon sheet is then removed from the film coater and placed in a mechanical press. Next, polyurethane foam is placed over the uncured, second layer of silicone material and, using the press set to 50 psi, the polyurethane foam is pressed into the uncured silicone for 1 minute, which results in a 70% integration. "% integration" as used herein refers to the percent of the thickness of the texturing material that the foam-like material is pressed into. The uncured silicone is then cured at 126° C. for 1 hour and acquires the texture of the polyurethane foam. The Teflon sheet is then peeled off of the cured silicone and discarded. The polyurethane foam is removed from the cured silicone by washing the polyurethane-silicone composite in 300 ml of 38% concentrated HCl for 5 minutes, followed by a 3-minute wash in distilled water. FIG. 2 shows the layers of material on the Teflon surface of the film coater: the "base material" is the first layer of silicone material; the "texturing material" is the second layer of silicone material which acquires the texture of the polyurethane foam.

Example 4

Using a press set to 60 psi, polystyrene-block-polyisoprene-block polystyrene ("polystyrene foam") is pressed into an uncured, 1 mm-thick sheet of a silicone material, such as MED-4810. The silicone is then cured at 100° C. for 2 hours, generating a cured silicone-polystyrene foam composite. A dilute second silicone material, which may be the same as or different from the first, such as MED-4810 dispersed in dichloromethane (10% w/w), is poured onto the cured silicone-foam; the cured silicone-foam coated with uncured silicone is immediately pressed for 5 seconds under a pressure of 40 psi between two Teflon or aluminum sheets. Next, the uncured silicone coating the cured silicone-foam is cured at 100° C. for 1 hour. The polystyrene foam is removed from the silicone by soaking the silicone in 200 ml of hexane overnight.

Example 5

First, a polyurethane sheet is completely submerged in a bath of silicone dispersed in xylene, for example, MED-4714 dispersed in xylene (10% w/w); the fully-submerged polyurethane sheet is pressed at 20 psi to enable the silicone dispersion to fully enter and saturate the polyurethane. The polyurethane sheet is then removed from the bath and excess silicone dispersion is allowed to run off of it. The silicone-polyurethane composite is then cured at 120° C. for one hour. The cured silicone-polyurethane composite is then pressed, at a pressure of 40 psi, into an uncured, 2 mm-thick sheet of a second silicone material, for example, MED-4815. The uncured second silicone material coating the cured silicone-polyurethane composite is cured at 120° C. for one hour, resulting in silicone that has acquired the foam-like texture of the polyurethane. The polyurethane is then removed from the silicone materials by dipping the silicone-polyurethane composite in DMSO (at 130° C.) for 20 minutes.

In some embodiments, suction can be used as an aid in integrating the foam-like material and the texturing material.

Suction can be applied to a foam-like material to pull the texturing material, for example, silicone in solvent, through the foam-like material. The more integrated the foam-like material and the texturing material, the thicker the foam-like texture that is created in the texturing material. Suction can also remove any excess texturing material, meaning texturing material beyond that which is sufficient to saturate the foam-like material, or texturing material that has not smoothly integrated into the foam-like material, but is instead blocking the pores of the foam-like material.

In some embodiments, the foam-like texture created in a texturing material, such as a silicone material, through the novel methods disclosed herein may be heterogeneous, as opposed to homogeneous. A "homogeneous" foam-like texture generally refers to a texture having approximately the same number of interconnections per pore (see Fig. for illustration of "interconnections"). A "heterogeneous" foam-like texture generally refers to a texture having variation in the number of interconnections per pore.

Figure 4A:
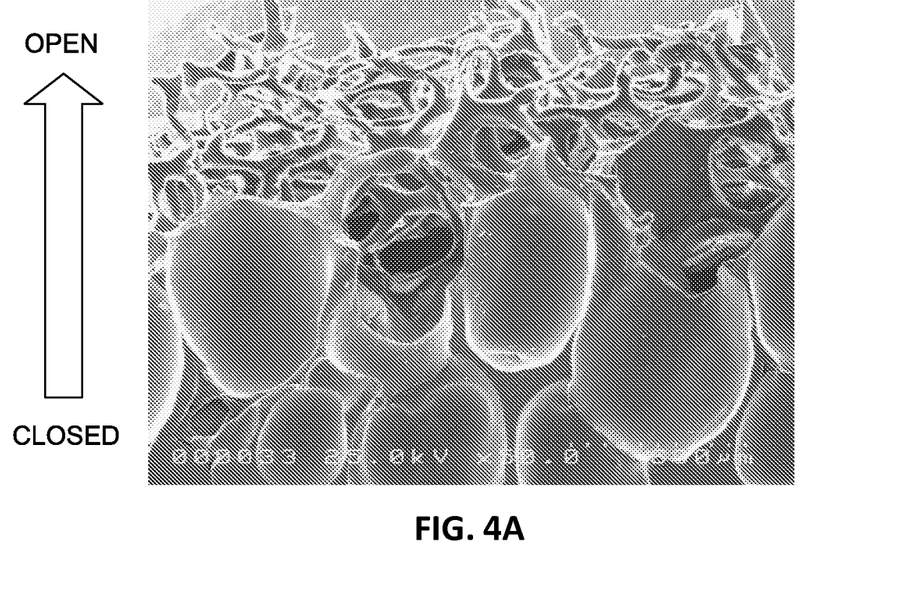
FIGS. 4A & 4B are SEM micrographs of the cross-sectional view of a silicone material, MED-6400, which has acquired a foam-like texture through the "sheet approach."
Figure 4B:
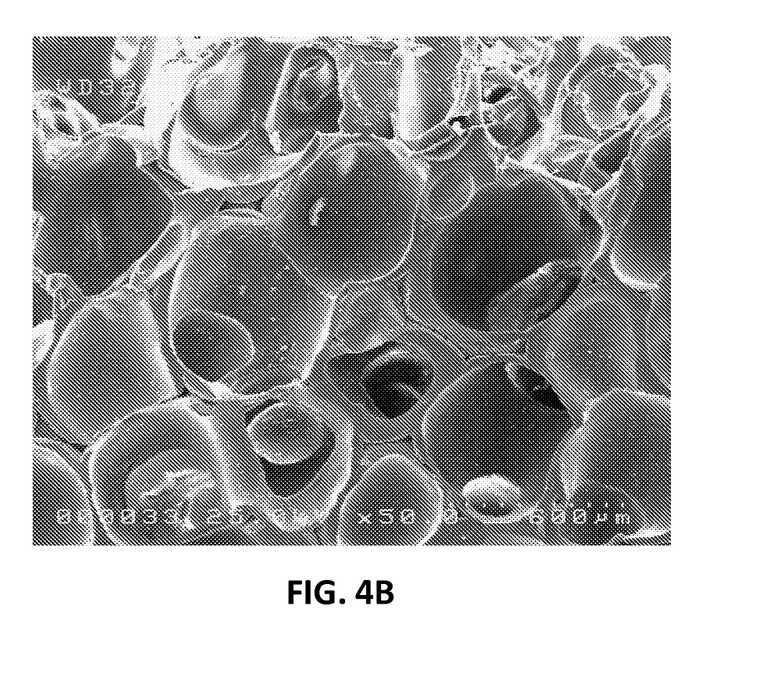
Figure 5:
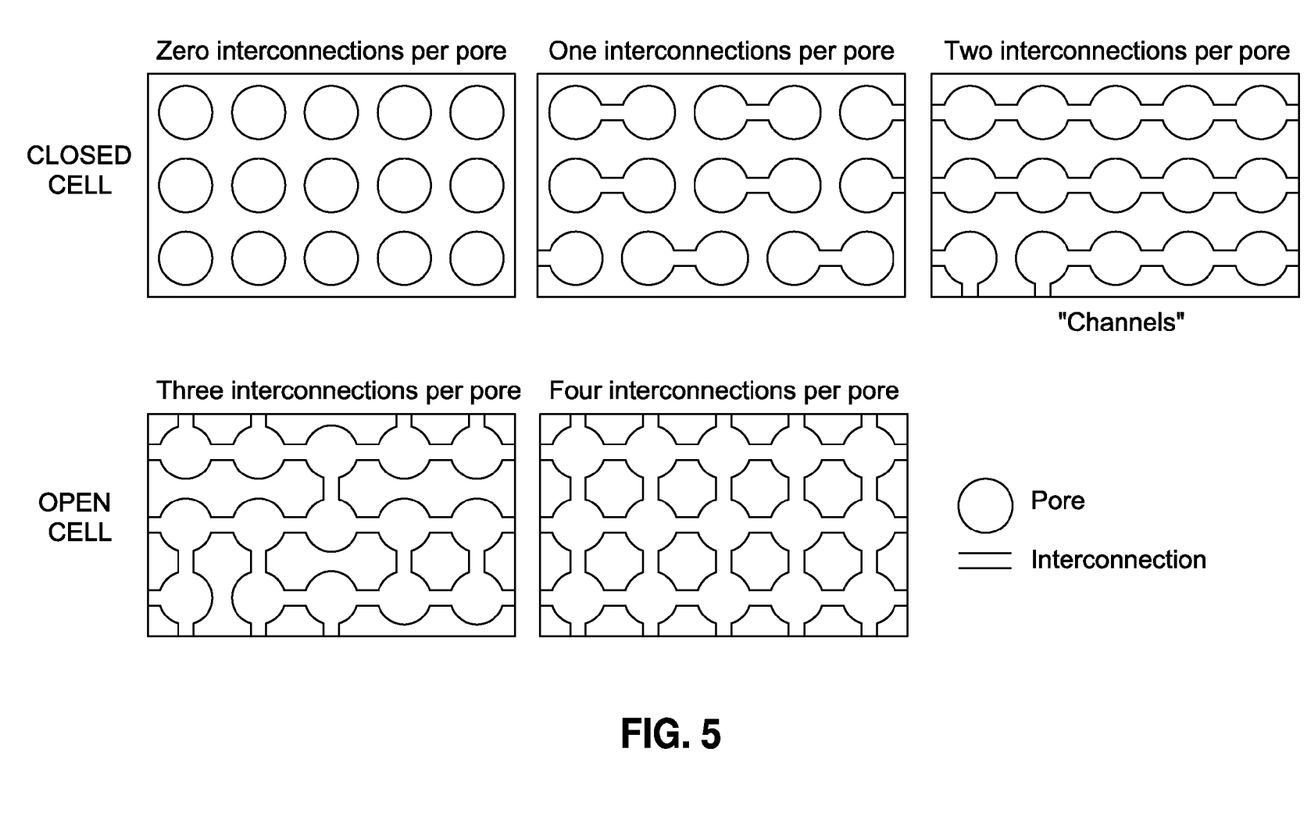
FIG. 5 is an illustration of open and closed cell foam structures.

An example of a heterogeneous foam-like texture that can be created in a texturing material would be a texture comprising a gradient of interconnections between pores: there is an increase in the number of interconnections per pore from one surface of the texturing material to the opposing surface (see FIG. 4A). In a cross section view, a texturing material having acquired a foam-like texture with a gradient of interconnections would resemble a closed cell foam at one end, but an open cell foam at the other end, with pores closer to the end resembling an open cell foam each having more interconnections than pores closer to the end resembling a closed cell foam (see FIG. 4A). A closed cell foam is generally characterized as having two or fewer interconnections per pore and an open cell foam as having three or more interconnections per pore (see FIG. 5).

For example, a heterogeneous foam-like texture can be created in a texturing material, such as silicone, if excess silicone, meaning more silicone than is necessary to saturate the foam-like material, is used. Because the silicone is in excess, the bottom surface of the silicone, which is the surface opposite the top surface onto which the foam-like material was pressed, would be a layer of silicone containing few or no pores; however, there are more and more pores and more interconnections per pore closer to the surface of the silicone onto which the foam-like material was pressed.

Whether and to what degree a texturing material acquires a heterogeneous foam-like texture can be due to many different factors, such as the amount of texturing material used relative to the foam-like material, the concentration of texturing material in solvent, the amount of pressure used to press the foam-like material and texturing material together, and changing the amount of solvent in which the texturing material is dispersed when the foam-like material is pressed against the texturing material.

The foam-like material used to impart a foam-like texture to a texturing material may have about 1% to about 99% porosity. As used herein, "% porosity" refers to % of the total volume of the foam-like material that comprise void or empty space. Consequently, a texturing material that has acquired a foam-like texture from a foam-like material may have about 1% to about 99% porosity.

The foam-like material may have a pore size of about 100-1000 μm (relative standard deviation ("RSD") of about 0.01-100%); an interconnection size of about 30-700 μm (RSD of 0.01-100%); interconnections per pore of about 2-20 (RSD of 0.01-50%); and an average pore to interconnection size ratio of about 3-99%.

In some embodiments, the foam-like material has a pore size of about 300-700 μm (RSD of 1-40%); an interconnection size of about 100-300 μm (RSD of 1-40%); interconnection per pore of about 3-10 (RSD of 1-25%) and an average pore to interconnection size ratio of about 10-99%.

In an exemplary embodiment, the foam-like material comprises a material, for example, polyurethane or other suitable material, having a pore size of 472+/−61 μm (RSD=13%), interconnection size of 206+/−60 μm (RSD=29%), interconnection per pore of 9.6+/−1.8 (RSD=19%), and pore to interconnection size ratio of 44%.

The texturing material can be solvent-free or dispersed in solvent when applied to a foam-like material for integration. One example of a texturing material that does not require dispersion in solvent is Room-Temperature-Vulcanizing silicone. The concentration of texturing material in solvent can range from about 5 to about 100% w/w. The greater the concentration of texturing material in solvent, the greater the density (mass per unit volume) of the end product, the texturing material which has acquired a foam-like texture, such as a silicone material that has acquired a foam-like texture. Non-limiting examples of useful solvents include acetone, xylene, dichloromethane, chloroform, dimethyl sulfoxide, water, methanol, methyl acetate, hexane, benzene toluene, and isopropyl alcohol.

The texturing material can be a solid, for example, an RTV silicone, or fluid material. Fluid materials include dispersions, solutions, emulsions, or a combination thereof. The viscosity of fluid texturing materials may range from approximately 10 to 3,000,000 cP.

Pressure applied to integrate a texturing material and foam-like material may range from 0.5 to 500 psi. In other embodiments, the pressure may range from 1 to 200 psi. Generally, the greater the pressure applied, the greater the degree of integration between the texturing material and the foam-like material, and the greater the extent and thickness of the foam-like texture layer that is created in the texturing material. Thus, the pressure can be varied depending on how extensive of a foam-like texture is desired to be created in the texturing material.

Figure 6A:
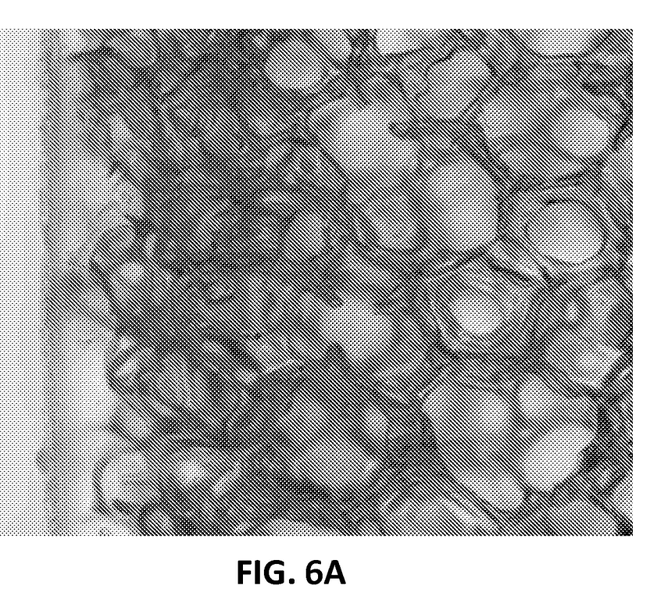
FIGS. 6A & 6B are SEM micrographs showing the foam-like texture of a silicone material, MED-2000, that acquired its foam-like texture from polyurethane foam under the high pressure of 100 psi. 6A is a cross-sectional view and 6B is a top view.
Figure 6B:
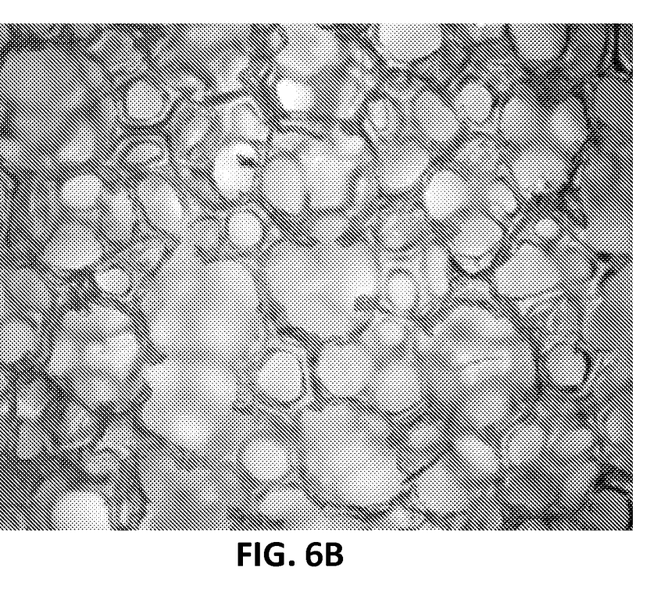

FIGS. 6A & 6B are SEM micrographs showing the foam-like texture of a silicone material, MED-2000, that acquired its foam-like texture from polyurethane foam under the high pressure of 100 psi. 6A is a cross-sectional view and 6B is a top view.

Figure 7A:
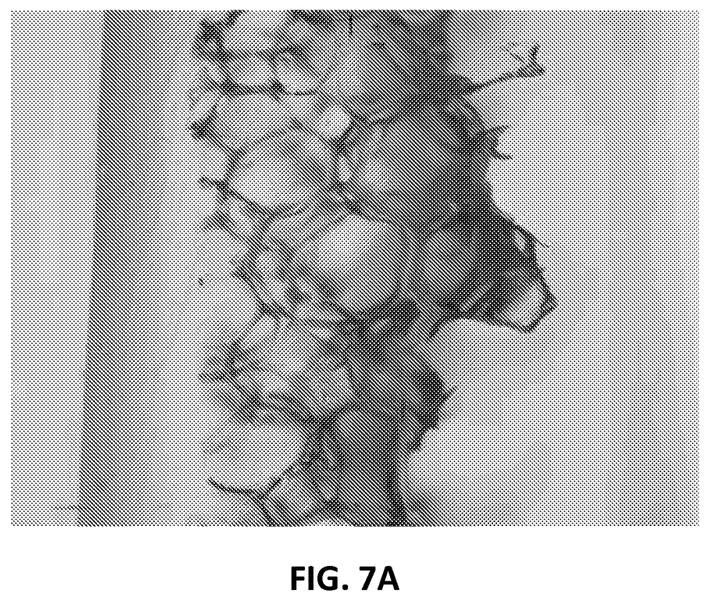
FIGS. 7A & 7B are SEM micrographs showing the foam-like texture of a silicone material, MED-2000, that acquired its foam-like texture from polyurethane foam under the low pressure of 10 psi. 7A is a cross-sectional view and 7B is a top view.
Figure 7B:
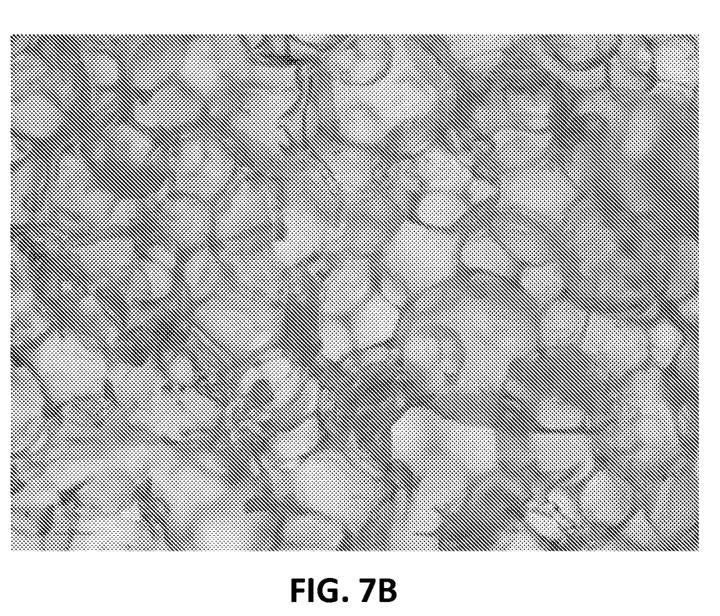

FIGS. 7A & 7B are SEM micrographs showing the foam-like texture of a silicone material, MED-2000, that acquired its foam-like texture from polyurethane foam under the low pressure of 10 psi. 7A is a cross-sectional view and 7B is a top view.

Because greater pressure was applied for the silicone texturing material shown in FIG. 6 than that shown in FIG. 7, there is a greater degree of integration for the one in FIG. 6 (compare, for example, the cross sectional images in 6A with that in 7A; the foam-like texture layer that is created is thicker in 6A than in 7A).

Also, the morphology of the foam-like material may change if too great a pressure is exerted to integrate the foam-like material and the texturing material, which would affect the foam-like texture that is created in the texturing material as well. What counts as too great a pressure depends on foam-like and texturing materials used; a set of foam-like and texturing materials pressed together under a certain pressure would result in the texturing material acquiring foam-like characteristics that differ from those it would acquire if pressed at a higher pressure.

If the texturing material used is dispersed in solvent, the type of solvent can affect the time it takes to integrate the texturing material and the foam-like material. For example, it generally takes less time to integrate a RTV silicone dispersed in dichloromethane with a foam-like material than a HTV silicone dispersed in xylene with a foam-like material.

Also, the foam-like material may swell when contacted with the solvent in which the texturing material is dispersed, and this can alter the texture of the foam-like material and hence the foam-like texture that the foam-like material imparts to the texturing material.

The process for removing the foam-like material after the foam-like material has imparted a foam-like texture to the texturing material varies depending on the foam-like material used. Any means known to those of skill the art and suitable for removing the foam-like material without substantially affecting the texturing material that has acquired a foam-like texture may be used. Agents used for removal may be a base, a solvent, an enzyme, an acid, heat, oxidation, uv light, gamma irradiation, visible light, infrared light or a combination thereof. When the foam-like material used is polyurethane, the polyurethane may be removed by, for example, dimethyl sulfoxide, hydrogen peroxide, hydrochloric acid, dimethyl formamide, acetone, or a combination thereof. The removing process may not remove all of the foam-like material all at once, so it may be repeated as desired.

The present invention also provides a method for creating one or more foam-like-textured surfaces on a breast prosthesis or implant. A textured material, having the desired dimensions, that acquires a foam-like texture through any of the novel methods described above, can be bonded, by a suitable, biocompatible adhesive, to a smooth shell breast prosthesis, to produce a breast prosthesis having a foam-like-textured surface.

In some embodiments, the methods disclosed hereinbefore may be used to create a foam-like texture on material that has already been textured through other means. For example, a texturing material, such as a silicone material, may undergo a texturing process as described in U.S. Pat. No. 5,007,929 ("Quaid patent"), which is incorporated by reference herein, before it undergoes any of the methods disclosed hereinbefore to acquire a foam-like texture.

In some embodiments, a breast implant may have a very thin, for example, 0.5 mm-thick, texturing material having a foam-like texture bonded to its front surface and a thicker, for example, 3 mm-thick, texturing material having a foam-like texture bonded to its back surface. Generally, the thickness of the texturing material having a foam-like texture used for bonding to surface(s) of breast implants can vary between approximately 0.1 to 50 mm. The foam-like material used to create texturing materials having a foam-like texture for bonding to surface(s) of breast implants can vary between approximately 0.1 to 250 mm thick.

What is claimed is:

1. A textured breast prosthesis comprising:
a silicone-based breast implant shell comprising a polyurethane-foam-like surface texture embossed over the entirety of said shell, said polyurethane-foam-like surface texture characterized by interconnected pores, wherein said foam-like surface texture comprises a gradient of interconnections between pores, and wherein said gradient of interconnections defining a closed cell foam at one end, and defining an open cell foam at an opposite end, with pores closer to the end defining an open cell foam each having more interconnections than pores closer to the end defining a closed cell foam, wherein the polyurethane-foam-like surface texture is configured to reduce capsular contracture, wherein said textured breast prosthesis is made by the steps of:
applying a base coat to a breast implant mandrel;
applying to the base coat, a texturing material comprising an uncured silicone dispersion;
placing a polyurethane foam sheet onto the silicone dispersion;
applying pressure to integrate the polyurethane foam and the silicone dispersion;
curing the silicone dispersion with the polyurethane foam integrated thereto;
after the step of curing, removing the polyurethane foam from the cured silicone by application of a solvent capable of dissolving polyurethane, to thereby obtain a textured breast implant shell.

2. The prosthesis of claim 1 wherein the thickness of the polyurethane foam sheet is between about 0.1 mm to about 250 mm.

3. The prosthesis of claim 1 wherein the thickness of the silicone dispersion is between about 0.1 mm to about 50 mm.

4. The prosthesis of claim 1 wherein the solvent is hydrochloric acid.

5. The prosthesis of claim 1 wherein the solvent is hexane.

6. The prosthesis of claim 1 wherein the solvent is dimethyl sulfoxide (DMSO).

7. A textured breast prosthesis comprising:
a silicone-based breast implant shell comprising a polyurethane-foam-like surface texture embossed over the entirety of said shell, said polyurethane-foam-like surface texture characterized by interconnected pores, wherein said foam-like surface texture comprises a gradient of interconnections between pores, and wherein said gradient of interconnections defining a closed cell foam at one end, and defining an open cell foam at an opposite end, with pores closer to the end defining an open cell foam each having more interconnections than pores closer to the end defining a closed cell foam, wherein the polyurethane-foam-like surface texture is configured to reduce capsular contracture, wherein said textured breast prosthesis is made by the steps of:
applying a texturing material onto a mandrel having the shape of a breast implant, wherein said texturing material comprises an uncured silicone dispersion;
placing a polyurethane foam sheet onto the texturing material;
causing integration between the texturing material and the polyurethane foam sheet by pressing the polyurethane foam sheet into the texturing material;
generating a composite of cured texturing material and polyurethane foam by curing the texturing material after the step of causing integration; and
after the step of generating the composite by curing, removing the polyurethane foam from the cured texturing material by application of a solvent of polyurethane to the composite, to thereby obtain a textured breast implant shell.

8. The prosthesis of claim 7, further comprising using clamps to stabilize the polyurethane foam sheet as it is placed onto and integrated with the texturing material.

9. The prosthesis of claim 7 wherein the thickness of the polyurethane foam sheet is between about 0.1 mm to about 250 mm.

10. The prosthesis of claim 7 wherein the thickness of the silicone dispersion is between about 0.1 mm to about 50 mm.

11. The prosthesis of claim 7 wherein the solvent is hydrochloric acid.

12. The prosthesis of claim 7 wherein the solvent is hexane.

13. The prosthesis of claim 7 wherein the solvent is dimethyl sulfoxide (DMSO).

* * * * *

UNITED STATES PATENT AND TRADEMARK OFFICE
CERTIFICATE OF CORRECTION

PATENT NO. : 9,155,613 B2  
APPLICATION NO. : 14/174133  
DATED : October 13, 2015  
INVENTOR(S) : Jordan Thompson et al.

Page 1 of 1

It is certified that error appears in the above-identified patent and that said Letters Patent is hereby corrected as shown below:

On The Title Page, Item (56)

On the Page 4, in column 1, under "Other Publications", line 2, delete "Anals" and insert -- Annals --, therefor.

In The Specification

In column 3, line 54, delete "ryon-triacetate," and insert -- rayon-triacetate, --, therefor.

In column 6, line 6, delete "maybe" and insert -- may be --, therefor.

In column 6, line 22, delete "HCI" and insert -- HCl --, therefor.

Signed and Sealed this  
Fifteenth Day of March, 2016

Michelle K. Lee  
*Director of the United States Patent and Trademark Office*